(12) United States Patent
Brosseau et al.

(10) Patent No.: US 6,450,978 B1
(45) Date of Patent: Sep. 17, 2002

(54) INTERACTIVE COMPUTER-ASSISTED SURGICAL SYSTEM AND METHOD THEREOF

(75) Inventors: Éric Brosseau, Montreal (CA); Michel Boivin, Montreal (CA); Geneviéve Hamel, Lasalle (CA); Louis-Philippe Amiot, Montréal (CA)

(73) Assignee: Orthosoft, Inc., Montreal (CA)

(*) Notice: Subject to any disclaimer, the term of this patent is extended or adjusted under 35 U.S.C. 154(b) by 0 days.

(21) Appl. No.: 09/322,398

(22) Filed: May 28, 1999

Related U.S. Application Data (60) Provisional application No. 60/087,089, filed on May 28, 1998, and provisional application No. 60/087,091, filed on May 28, 1998.

(51) Int. Cl.$^7$ ................................................. A61B 5/00
(52) U.S. Cl. ........................................................... 600/595
(58) Field of Search .................................. 600/587, 592, 600/594, 595; 606/53, 54, 86–89, 96, 97

(56) References Cited

U.S. PATENT DOCUMENTS

| | | | |
|---|---|---|---|
| 4,608,977 A | 9/1986 | Brown | 128/303 B |
| 4,618,978 A | 10/1986 | Cosman | 378/164 |
| 4,674,046 A | 6/1987 | Ozeki et la. | 364/414 |
| 4,791,934 A | 12/1988 | Brunnett | 128/653 |
| 4,805,615 A | 2/1989 | Carol | 128/303 |
| 4,841,975 A | 6/1989 | Woolson | 128/653 |
| 4,882,679 A | 11/1989 | Tuy et al. | 364/413.22 |
| 5,086,401 A | 2/1992 | Glassman et al. | 395/94 |
| 5,099,846 A | 3/1992 | Hardy | 128/653.1 |
| 5,155,435 A | 10/1992 | Kaufman et al. | 324/309 |
| 5,236,432 A | 8/1993 | Matsen, III et al. | 606/88 |
| 5,360,446 A | 11/1994 | Kennedy | |
| 5,526,812 A | 6/1996 | Dumoulin et al. | 128/653 |
| 5,564,437 A | 10/1996 | Bainville et al. | 128/774 |
| 5,682,886 A | 11/1997 | Delp et al. | 128/653.1 |
| 5,695,501 A | 12/1997 | Carol et al. | 606/130 |
| 5,715,836 A | 2/1998 | Kliegis et al. | 128/898 |
| 5,734,384 A | 3/1998 | Yanof et al. | 345/424 |
| 5,748,767 A | 5/1998 | Raab | 382/128 |
| 5,769,092 A | 6/1998 | Williamson, Jr. | 128/898 |
| 5,782,764 A | 7/1998 | Werne | 600/411 |
| 5,792,147 A | 8/1998 | Evans et al. | 666/138 |
| 5,824,085 A | 10/1998 | Sahay et al. | 623/16 |
| 6,194,095 B1 | 2/2001 | Hockaday | |
| 6,224,373 B1 | 5/2001 | Lee et al. | |

FOREIGN PATENT DOCUMENTS

| | | |
|---|---|---|
| DE | 4225112 | 12/1993 |
| DE | 29704393 | 8/1997 |
| WO | WO 96/10949 | 4/1996 |
| WO | WO 97/29710 | 8/1997 |
| WO | WO 99/23956 | 5/1999 |

OTHER PUBLICATIONS

Computer–Aided Image–Guided Bone Fracture Surgery: Modeling, Visualization, and Preoperative Planning, Medical Image Computing and Computer–Assisted Intervention–MICCA '98 pp. 29 to 38;.

(List continued on next page.)

*Primary Examiner*—Max Hindenburg
(74) *Attorney, Agent, or Firm*—Wells St. John P.S.

(57) ABSTRACT

A computer-assisted surgical system and method are described herein. The computer-assisted surgical system comprises a computer including three-dimensional models of anatomical structures and a user interface including a position sensing system to register in real-time the relative positions of the anatomical structures of interest and of a surgical tool. Interactions between the tool and the anatomical structure are displayed on a monitor using the three-dimensional models. Multi-view display, transparency display and use of cutting planes allow the surgeon to visualize the interaction between the tool and the anatomical structures any time during the surgical procedure. The system can also predict the constraint on anatomical structures before surgery.

21 Claims, 4 Drawing Sheets-

OTHER PUBLICATIONS

Computer–Aided Planning of Patellofemoral Joint OA Surgery: Developing Physical Models from Patient MRI, Medical Image Computing and Computer–Assisted Intervention—MICA '98, pp. 9 to 20;.

Planning and Evaluation of Reorienting Osteotomies of the Proximal Femur in Cases of SCFE Using Virtual Three–Dimensional Models, Medical Image Computing and Computer–Assisted Intervention—MICCA '98 pp. 1 to 8;.

A Surgical Planning and Guidance System for high Tibial Osteotomies, Medical Image computing and Computer–Assisted Intervention—MICCA '98, pp. 39 to 50;.

Effects of Tracking Adjacent Vertebral Bodies During Image Guided Pedicle Screw Surgery, CVR Med—MRCAS '97, Grenoble, France, pp. 531–540;.

Development and Validation of a Navigational Guidance System for Acetabular Implant Placement, CVR Med—MRCAS '97, pp. 582–592;.

Accuracy of Image Guided Placement of Iliosacral Lag Screws, CRV Med—MRCAS '97, pp. 593 to 596;.

A System for Computer Assisted Arthroscopy, CVR Med—MRCAS'97, Grenoble, France, pp. 653–662;.

Computer–Assisted Knee Surgical Total Replacement, CVR Med—MRCAS '97, Grenoble, France, pp. 629–638;.

Computer Asisted Planning for Tital Knee Arthroplasty, CVR Med—MRCAS'97, Grenoble, France, pp. 619–628.

Amiot, Louis–Philippe et al., "Com puter–Assisted Pedicle Screw Fixation", *SPINE*, Bol. 20, No. 10, pp. 1208–1212 (1995).

Marcus Richter, et al., "Computer–assisted surgery in posterior instrumentation of the cervical spine: an in–vitro feasibility study", Nov. 16, 1999, Eur Spine J (2000) 9 (Suppl 1):S65–S70.

Louis–Philippe Amiot, MD, et al., "Comparative Results Between Conventional and Computer–Assisted Pedicle Screw Installation in the Thoracic, Lumbar, and Sacral Spine", Mar. 2000, SPINE, vol. 25, No. 5, pp. 606–614.

L.P. Amiot, et al., "Installation de vis pédiculaires par ordinateur", Annales de Chirurgie, 1996, 50, n° 8, pp. 626–630.

Amiot, L.Ph., et al., "Évaluation *in vitro* d'un système informatique de forage pédiculaire", Annales de Chirurgie, 1997, 51, n° 8, pp. 854–860.

INTERACTIVE COMPUTER-ASSISTED SURGICAL SYSTEM AND METHOD THEREOF

CROSS REFERENCE TO RELATED APPLICATIONS

Priority is claimed from an earlier filed U.S. Provisional Patent Application No. 60/087,089, filed May 28, 1998, for "Interactive Computer-Assisted Surgical System and Method Thereof" by Eric Brosseau, Michel Boivin and Genevieve Hamel, and from an earlier filed U.S. Provisional Patent Application No. 60/087,091, filed May 28, 1998, for "Interactive Computer-Assisted Surgical System and Method Thereof", by Eric Brosseau, Michel Boivin and Genevieve Hamel.

FIELD OF THE INVENTION

The present invention relates to computer-assisted surgical systems. More specifically, the present invention is concerned with an interactive computer-assisted surgical system and method thereof.

BACKGROUND OF THE INVENTION

Computer-assisted surgical systems are used to help doctors during a surgical procedure. Initially, these systems were only displaying status and data on the patient's physical condition. Eventually, computer-assisted surgical systems have evolved to allow real-time interaction between the surgeon procedures and the computer data displayed. In recent years, computer-assisted surgical systems began displaying computer generated models of the anatomical structures of interest to help the surgeon visualize the surgical procedure being performed.

One such system has been described by Willie Williamson, Jr. in U.S. Pat. No. 5,769,092, issued on Jun. 23, 1998. In this patent, Williamson teaches a computer-assisted system to help perform a hip replacement. The system allows the surgeon to interact with three-dimensional models of the relevant bones to select an appropriate replacement strategy. A first drawback of Williamson's system is that there is no registration of the anatomical structures of interest and thus, these anatomical structures must be adequately immobilized in order to visualize the interaction between the structures and a robotic arm. The immobilization of the anatomical structures renders the intra-operating room planning difficult, since no trial movements can be performed on the immobilized structures. Furthermore, only the movements of the robotic arm are reproduced on the display monitor and the interaction is performed only on two-dimensional images of the anatomical structures. Finally, Williamson's system does not allow the visualization of transparent three-dimensional models of the anatomical structures.

In the U.S. Pat. No. 5,682,886, issued on Nov. 4, 1997, Scott L. Delp et al., propose a computer-assisted surgical system that overcomes some drawbacks of Williamson's system. Delp teaches the interaction of a surgical tool with three-dimensional models of the anatomical structures of interest. However Delp's system does not allow real-time update of the positions of both the surgical tool and the three-dimensional models. Furthermore the registration process requires a lot of inputs from the surgeon. Another drawback of Delp's system is that the three-dimensional models do not appear partially transparent on the display monitor. Thus, the anatomical structures may obstruct the view of the tool, depending on the relative position of the tool and the anatomical structures or the tool may simply be overlaid over the three-dimensional model, providing partial occlusion of the structures. As discussed hereinabove with respect to Williamson's system, Delp's system does not allow intra-operating room planning.

Improved computer-assisted surgical system and method are thus desirable.

OBJECTS OF THE INVENTION

An object of the present invention is therefore to provide computer-assisted surgical system and method free of the above mentioned drawbacks of the prior-art.

Another object of the invention is to provide computer-assisted surgical system and method that allow real-time registration of a surgical tool on transparent three-dimensional models of anatomical structures.

Still another object of the present invention is to provide computer-assisted surgical system and method that allow real-time display of the relative positions of transparent three-dimensional models of anatomical structures and of a surgical tool.

SUMMARY OF THE INVENTION

More specifically, in accordance with the present invention, there is provided an interactive surgical system to assist a surgery on at least one anatomical structure, the system comprising:

a tool;

a computer, including a three-dimensional model of each of the at least one anatomical structure and a three-dimensional model of the tool;

an output device connected to the computer; the output device being configured to display the model of each of the at least one anatomical structure and the model of the tool; and a position sensing system connected to the computer; the position sensing system being configured to register the position of the tool and the position of each of the at least one anatomical structure and transferring the positions to the computer; whereby, in operation, the computer, using the positions of the tool and of the at least one anatomical structure, is configured to determine virtual positions of the models of each of the at least one anatomical structures and of the tool and to control the output device to display the models of each of the anatomical structure and of the tool at their respective virtual positions; the three-dimensional model of each of the at least one anatomical structure being so displayed as to appear partially transparent.

According to another aspect of the present invention, there is provided an interactive user interface for a computer system to assist a surgery on an anatomical structure, the user interface comprising:

a tool;

an output device connected to the computer; the output device being configured to display a three-dimensional model of each of the at least one anatomical structure and a three-dimensional model of the tool; and a position sensing system connected to the computer; the position sensing system being configured to register the position of the tool and the position of each of the at least one anatomical structure and to transfer these positions to the computer; whereby, in operation, the computer, using the positions of the tool and of the at least one anatomical structure, is configured to determine virtual positions of the models of each of the at least one anatomical structures and of the tool and to control the output device to display the models of each of the anatomical structure and of the tool at their respective virtual positions.

According to another aspect of the present invention, there is provided a method to assist a surgical procedure on at least one anatomical structure, the method comprising:

providing a position sensing system;

providing a tool to perform a surgical procedure on the at least one anatomical structure;

using the position sensing system to register the relative position of the tool and of each of the at least one anatomical structure;

using the relative position of the tool and of each of the at least one anatomical structure to compute respective virtual positions of each of the at least one anatomical structure and of the tool;

providing an output device;

displaying on the output device a first view including a transparent three-dimensional computer model of each of the at least one anatomical structure and a three-dimensional computer model of the tool at the respective virtual positions.

According to yet another aspect of the present invention, there is provided a method of determining the appropriate position of a surgical implant on at least one anatomical structure, the method comprising:

identifying a possible position for the implant on the at least one anatomical structure;

registering the possible position for the implant and the position of each of the at least one anatomical structure;

creating a computer models of each of the at least one anatomical structure with the implant;

placing the at least one anatomical structure in at least one position;

registering the at least one position of the anatomical structure; and using the at least one registered position to simulate constraints on at least one of the at least one anatomical structure and the implant;

wherein the appropriate position is one of the at least one position where the simulated constraint lies in a predeterminate acceptable range.

Finally, according to another aspect of the present invention, there is provided a computer-assisted surgical system to assist in the installation of an implant on at least one anatomical structure, the system comprising:

a tool to identify a possible position for the implant on the at least one anatomical structure;

a computer including models of each of the at least one anatomical structure and of the implant;

a position sensing system connected to the computer; the position sensing system being configured to register the possible position for the implant with respect to at least one position of each of the at least one anatomical structure and to transfer the positions to the computer; and whereby, in operation, the computer simulates constraints for each of the at least one position of each of the at least one anatomical structure;

wherein an appropriate position of the implant is one of the at least one position where the simulated constraint lies in a predeterminate acceptable range.

Other objects, advantages and features of the present invention will become more apparent upon reading of the following non restrictive description of preferred embodiments thereof, given by way of example only with reference to the accompanying drawings.

DESCRIPTION OF THE PREFERRED EMBODIMENT

Figures 1, 2:
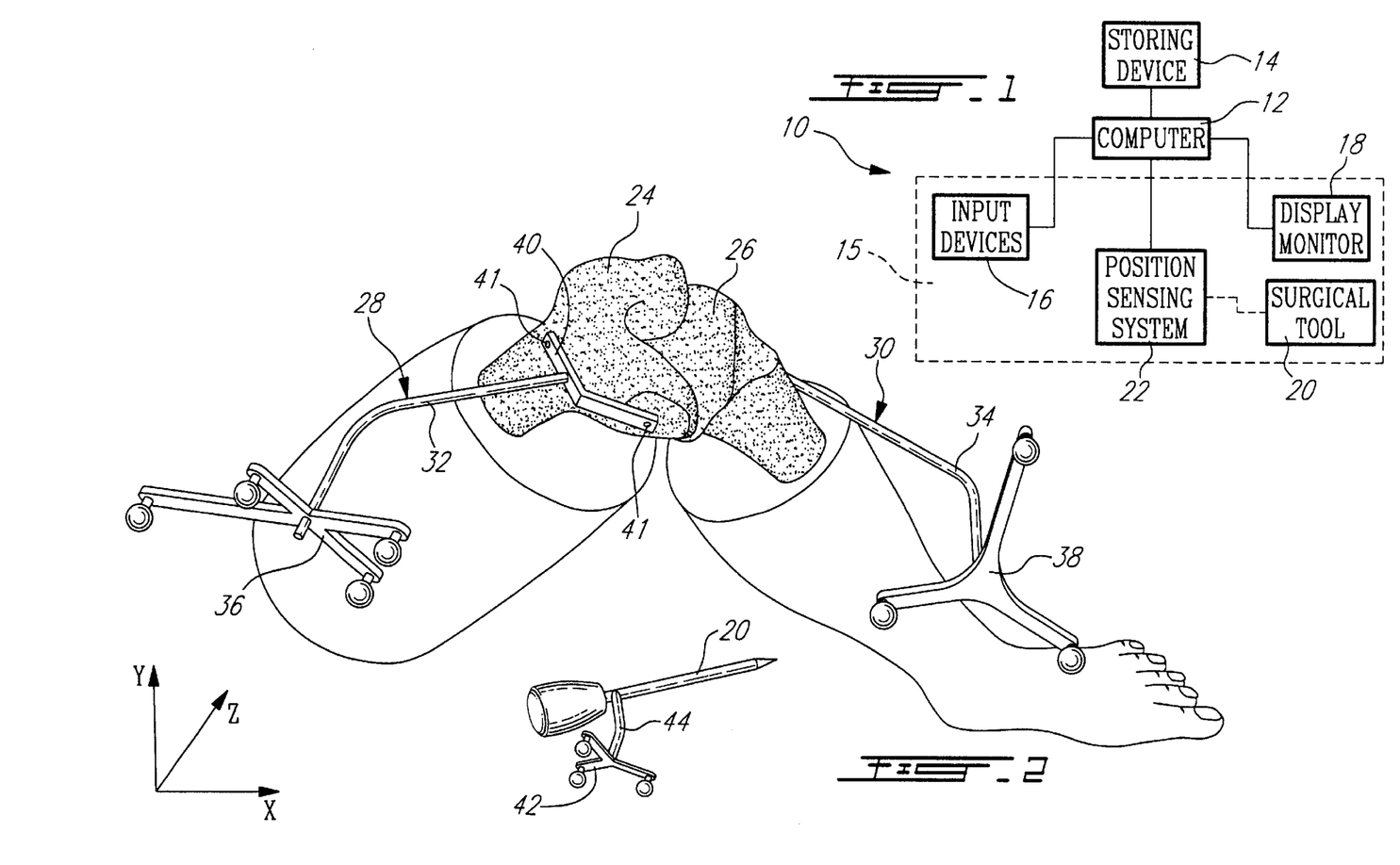
FIG. 1 is a bloc diagram of an interactive computer-assisted surgical system according to an embodiment of the present invention.
FIG. 2 is a schematic perspective view of a surgical tool and of a human knee with reference clamps mounted thereto.

Turning now to FIG. 1 of the appended drawings, an interactive computer-assisted surgical system 10 to perform a surgical procedure on anatomical structures will be described.

The system 10 comprises a computer 12 having a memory (not shown), a storing device 14 and a user interface 15. The user interface 15 includes input devices 16, an output device in the form of a display monitor 18, a surgical tool 20 and a position sensing system 22.

The storing device 14 is used to store three-dimensional models of the surgical tool 20 and of the anatomical structures, in this case, in the form of a femur 24 and a tibia 26, (see FIG. 2) on which a surgical procedure is to be performed. The storing device 14 can take any form well known by a person of ordinary skills in the art: a hard disk drive, a disk drive, a CD-ROM drive, another computer's memory, etc. The storing device 14 can be directly connected to the computer 12 via conventional peripheral connectors, such as, for example, cables or an infrared connection, or remotely via a computer network, such as, for example, the Internet.

In a preferred embodiment of the present invention, the input devices 16 are in the form of a keyboard and a mouse. The input devices 16 allow the user to enter commands to the computer 12, in order, for example, to select display options. Although the system 10 is described with two input devices 16, only one can be used without departing from the spirit of the present invention. The input devices 10 can also take other forms, such as, for example a touch screen or a voice recognition system.

Although the present invention is described with a display monitor as the output device 18, a person of ordinary skills in the art can conceive a similar system, using another type of output device 18, such as, for example, three-dimensional display goggles, without departing from the spirit of the present invention.

The surgical tool 20 can be, for example, an awl, a screwdriver to install, for example, an artificial ligament, or any tool used in surgical procedures.

Turning briefly to FIG. 2 of the appended drawings, the position sensing system 22 will be described in further details. The position sensing system 22 includes a position sensing device, in the form of a video camera (not shown), connected to the computer 12 via conventional connectors and reference clamps 28 and 30, secured respectively to the patient's femur 24 and tibia 26. Position sensing systems are believed well known to persons of ordinary skills in the art, and thus, will now be described only briefly.

The reference clamps 28 and 30 include bended rods 32,34 and reference assemblies 36 and 38, secured to their respective rods 32 and 34. Reference assemblies 36 and 38 are of different shapes so that they can be discriminated by the computer 12. Each of reference clamps 28 and 30, also includes mounting brackets 40 (only one shown) to adequately secure the reference clamps to the tibia 24 and the femur 26, using small surgical screws 41 (only two shown).

Similarly, a reference assembly 42 is secured by welding to the surgical tool 20 via a bended rod 44. It is to be noted that the reference assembly 42 may, alternatively, include a mounting bracket to secure the reference assembly 42 on other surgical tools.

The operation of the position sensing system 22 will now be described. The camera is used to capture and to transfer to the computer 12 the image of the reference assemblies 36,38 and 42 during the surgical procedure. A registration algorithm, including conventional registration method, is used to convert the realtime image in relative position between each of the reference assemblies 36, 38 and 42. Since the position, shapes and size of each reference assemblies 36,38 and 42 are known to the computer 12, the relative position of the surgical tool 20 with respect to the anatomical structures 24 and 26 may be calculated.

The position sensing system 22 may also include a dedicated processor (not shown) that can determine the relative positions of the reference assemblies 36, 38 and 42 and/or the relative positions of the surgical tool 20 and anatomical structures 24 and 26 before sending that information to the computer 12.

Other well known position sensing systems, such as, for example, a magnetic position sensing system, can also be used. In such a system, the camera is advantageously replaced by a magnetic field sensor and the reference assemblies are advantageously replaced by magnetic field emitters.

It is to be noted that it may be advantageous to include a connection between the surgical tool 20 and the position sensing system 22, when using certain position sensing systems 22.

It is also to be noted that, if the surgical tool 20 includes moving parts, individual reference assemblies must be secured to each of those moving parts in order to enable the display of relative positions.

Figure 3:
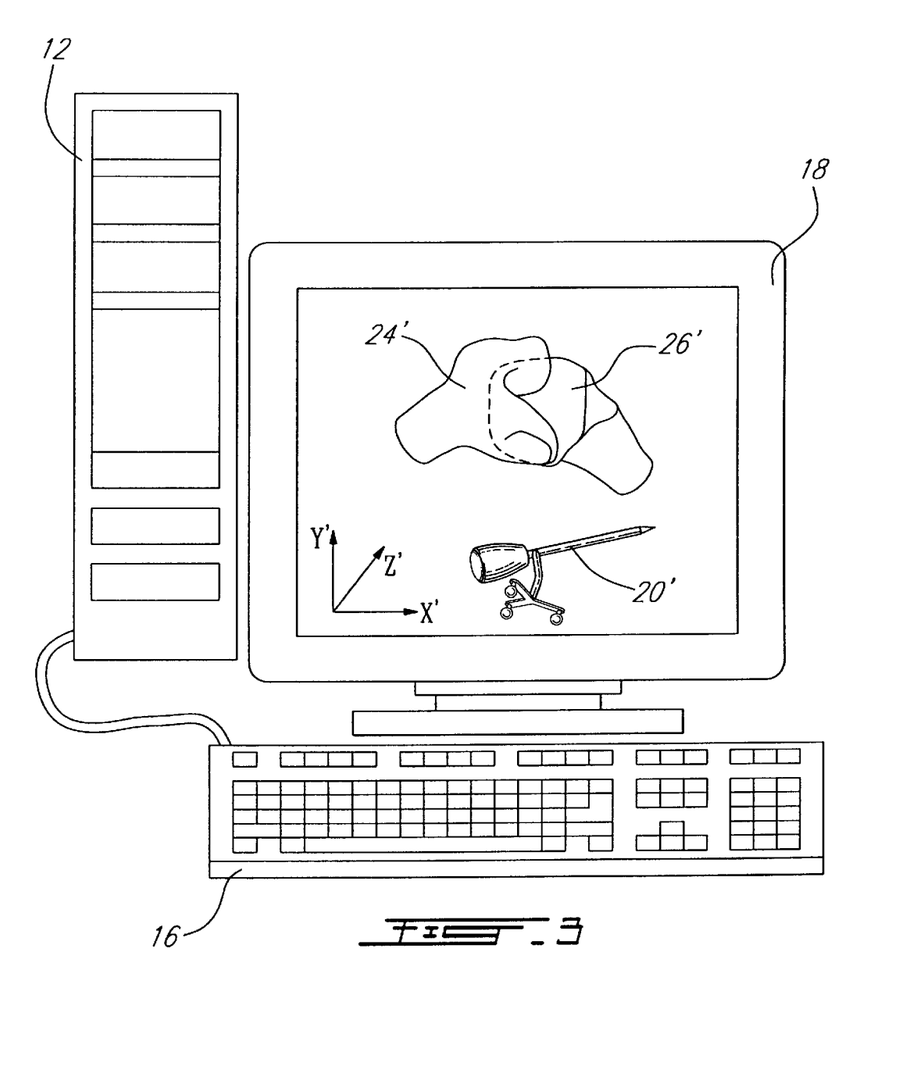
FIG. 3 is a schematic view of the interactive computer-assisted system of FIG. 1 without the position sensing system.
Figure 4:
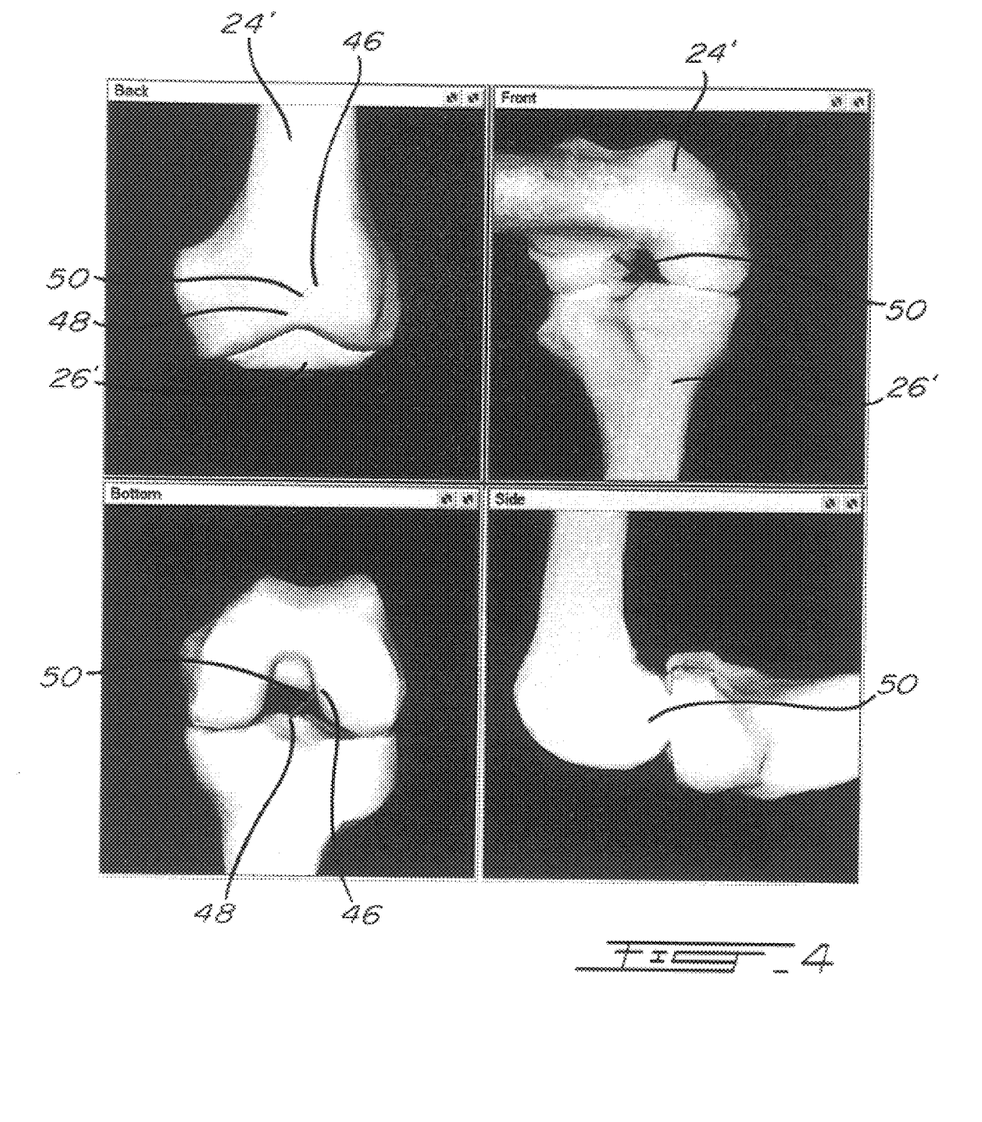
FIG. 4 is a screen shot illustrating different points of view of three-dimensional models of anatomical structures displayed by the system of FIG. 1.
Figure 5:
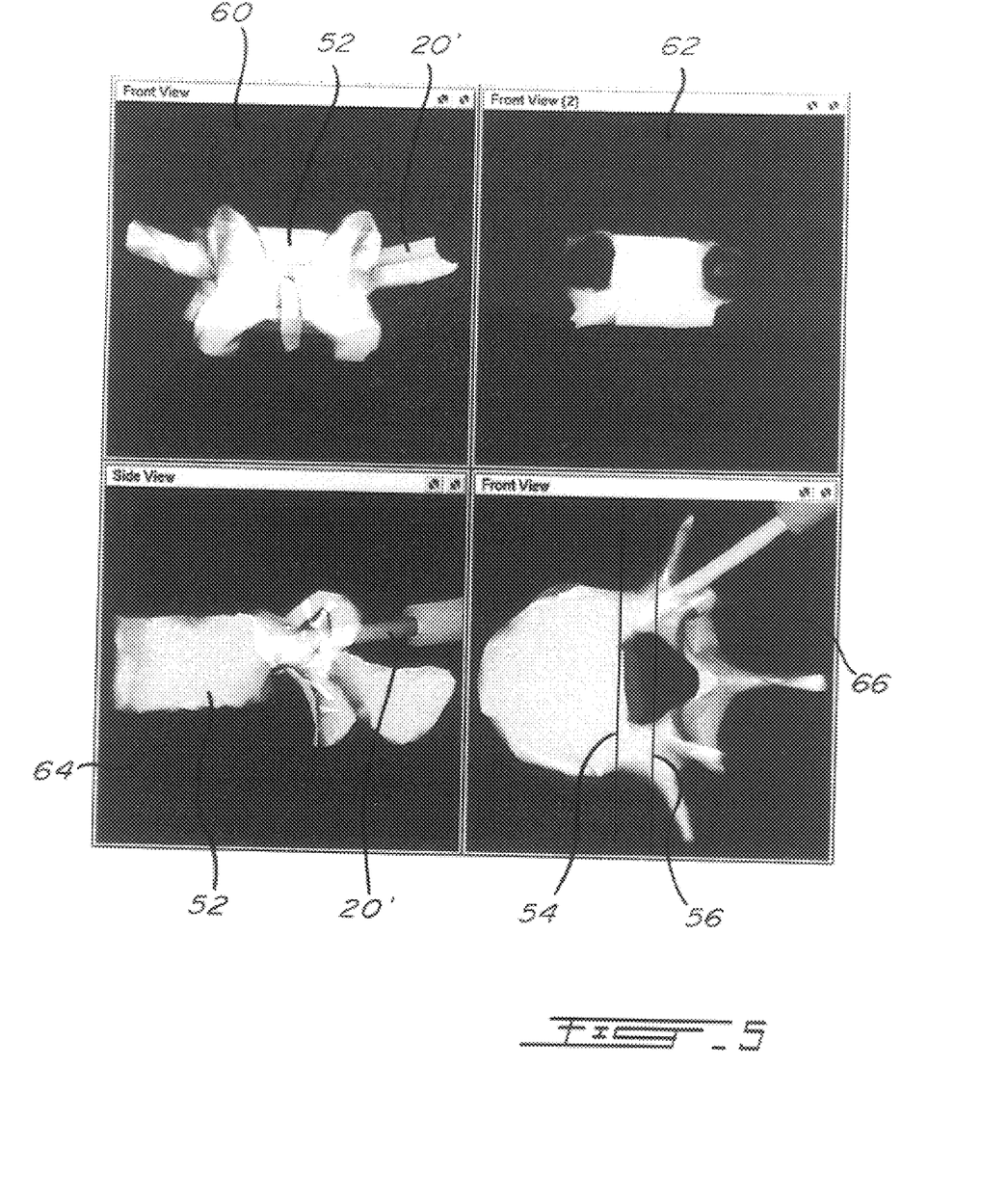
FIG. 5 is a screen shot illustrating the interaction between three-dimensional models of an anatomical structure and of a surgical tool, as displayed by the system of FIG. 1.

Turning now to FIGS. 3, 4 and 5 of the appended drawings, the general features of a computer-assisted surgical method according to an aspect of the present invention will be described.

The first step of the method is to provide the computer 12 with three-dimensional models of the tibia 24, the femur 26 and the surgical tool 20. These models are transferred from the storing device 14 to the computer memory. The three-dimensional models could have been obtained, for example, from two-dimensional slice images of the anatomical structures of interest, using three-dimensional reconstruction systems. Three-dimensional reconstruction systems are believed well known by a person of ordinary skills in the art and thus will not be described furthermore. Other means can also be used to provide three-dimensional models of the anatomical structures and of the surgical tools, without departing from the spirit of the present invention. The slice images can be obtained, for example, by scanning the anatomical structures with a CT or a MRI scanner.

The second step is to calibrate the surgical tools 20 and the reference clamps 28 and 30. For example, this is accomplished by the computer 12, by performing transformations, first, from the reference assembly 42 to the tip of the surgical tool 20 and second, by selecting reference points on the three-dimensional models of the anatomical structures 24, 26 and by identifying the corresponding points on the anatomical structures 24 and 26. Of course, other calibration protocols could be used.

During the surgical procedure, the position sensing system 22 will first register the positions and orientations of the reference assemblies 36,38 and 42 in the coordinate system of the position sensing system (represented by the axes X, Y and Z in FIG. 2). Then the orientations and positions of the surgical tool 20, the tibia 24 and the femur 26 are transformed into virtual orientations and position in the reference system of the three-dimensional models, represented by the axes X', Y' and Z' in FIG. 3. The three-dimensional models of the tool 20 and of the anatomical structures 24 and 26, denoted 20', 24' and 26' in FIGS. 3–5, are then reproduced on the display monitor 18 in their new orientations and at their new positions in the computer reference system.

The registration process by the position sensing system 22 and the regeneration of the image on the display monitor 18 are performed at a rate sufficient to allow real-time display and interaction with the three-dimensional models 24' and 26'. The display is said to be in real-time, since movement of the models is perceived as being continuous, without flicker effect, and synchronized with the movements of the anatomical structures 24, 26 and of the surgical tool 20.

The computer 12 is programmed to allow visualization of the anatomical structures 24' and 26' and of the surgical tools 20' as it would be seen from different points of view. FIG. 4 of the appended drawings illustrates four such views that can be simultaneously displayed on the display monitor 18. The different points of view can be selected using the input devices 16.

The computer 12 is also programmed to display the anatomical structures 24' and 26' as translucent (partially transparent) objects. The surgeon can therefore always visualize the interaction between the surgical tool 20 and the anatomical structures 24' and 26' since the surgical tool 20 is never occluded by the anatomical structures 24' and 26'. Software programs that allow visualization of translucency and visualization of three-dimensional objects from different points of view are believed well known by a person of ordinary skills in the art and will not be described in further details.

In order to illustrate other features of the method of the present invention, a method of planning the installation of a surgical implant, while the patient is under sedation, using the system 10 will now be described. The example chosen to illustrate the method is the replacement of the Anterior Cruciate Ligament (ACL) of the knee by an artificial ligament.

It is well known by surgeons specialized in knee surgery that the artificial ligament that joints the femur to the tibia should be placed in such a way that it respects an isometry constraint. The present system allows to virtually position a virtual ligament 50 in order to assess such constraint prior to the surgical procedure.

The surgeon uses the surgical tool 20, in the form of an awl, to identify on the patient's tibia 24 and femur 26 the two points 46 and 48 where he believes he should place the artificial ligament. From those two points, a virtual model of the ligament 50 is created by the computer 12 and displayed on the monitor 18 with the models of the tibia 24' and femur 26'. (It is to be noted that the calibration step described hereinabove must be performed before the planning procedure.) As will become apparent upon reading the description of the following example, the planning procedure makes use of the features of the above described system and method.

The surgeon then flexes the patient's knee in order to obtain a set of position measurements. As it has been described hereinabove, the positions of the tibia 24 and of the femur 26 will be determined by the computer 12 and displayed as tibia 24' and femur 26' onto the monitor 18.

According to these positions, the computer 12 will calculate the distance between the two specified points at different flexion angles. A message is then displayed on the monitor 18, informing the surgeon whether or not the isometry constraint is respected. If the constraint is not within a pre-specified tolerance, the surgeon may change the proposed artificial ligament position and perform another leg flexion to verify isometry. Once a position is found satisfying, the surgeon can use the system 10 to perform the surgical procedure. More specifically, the surgeon can visualize the positions of the two points 46 and 48 on the three-dimensional computer models displayed on the monitor to guide him while drilling the holes that will be used to fix the artificial ligament 50.

Turning now to FIG. 5 of the appended drawings, other features of the system and method, according to the present invention, will be described.

FIG. 5 illustrates the use of the interactive computer-assisted surgical system 10 to perform a surgical procedure on a lumbar vertebra 52.

One can see in FIG. 5 four different views 60, 62, 64 and 66 of the three-dimensional models of a lumbar vertebra 52 and of the surgical tool 20. In this example, the surgical tool is in the form of a screwdriver.

Again, the use of transparency to display the three-dimensional model of the anatomical structure, here in the form of a lumbar vertebra 52, allows the surgeon to visualize the tip of the surgical tool 20', even though it is inserted in one of the cavities of the lumbar vertebra 52.

In addition to select different view points and display simultaneously the three-dimensional models according to those views, using the input device 16, the surgeon can also select cutting planes (see line 54 and 56 on view 66 of FIG. 5) from which the anatomical structure is to be seen. The use of the cutting planes 54 and 56 indicates the correspondence between different views of the same anatomical three-dimensional model and thus helps the surgeon in performing surgical navigation. For example, view 62 is taken from line 56.

According to a preferred embodiment of the present invention, it is possible for the surgeon to choose the transparency intensity, ranging from opacity to disappearance of the models, used to display the three-dimensional models of the anatomical structure 52.

It is to be noted that it is possible to display simultaneously two and three-dimensional representations and views of the anatomical structures and of the surgical tool without departing from the spirit of the present invention. The number of views displayed simultaneously may also vary.

In a preferred embodiment of the present invention, a mouse is used to select view points and cutting planes on the three-dimensional model of the anatomical structures. Of course, other input devices could be used.

The anatomical structure can be any part of the human anatomy from which a computer three-dimensional model can be obtained. The structure must however have sufficient rigidity to allow registration of its position.

Although the present invention has been described hereinabove by way of preferred embodiments thereof, it can be modified, without departing from the spirit and nature of the subject invention as defined in the appended claims.

What is claimed is:

1. An interactive surgical system to assist a surgery on at least one anatomical structure, said system comprising:
    a tool;
    a computer, including a three-dimensional model of each of the at least one anatomical structure and a three-dimensional model of said tool;
    an output device being configured to display said model of each of the at least one anatomical structure and said model of said tool; and
    a position sensing system being configured to register the position of said tool and the position of each of the at least one anatomical structure and transferring said positions to said computer;
        wherein, in operation, said computer, using said positions of said tool and of the at least one anatomical structure, is configured to determine virtual positions of said models of each of the at least one anatomical structures and of said tool and to control said output device to display said models of each of said anatomical structure and of said tool at their respective virtual positions; said three-dimensional model of each of the at least one anatomical structure being so displayed as to appear partially transparent, the computer being further configured to selectively vary the transparency intensity used to display said three-dimensional model, ranging from opacity to disappearance of the model.

2. An interactive surgical system as recited in claim 1, further comprising a storing device, connected to said computer, to store at least one of said model of the at least one anatomical structure and said surgical tool.

3. An interactive surgical system as recited in claim 2, wherein said storing device is taken from the group consisting of a disk drive, a CD-ROM drive, a hard-disk drive and a computer memory.

4. An interactive surgical system as recited in claim 2, wherein said storing device is remotely connected to the computer via a computer network.

5. An interactive surgical system as recited in claim 1, wherein said position sensing system includes:
    at least one magnetic field emitter secured to the at least one anatomical structure;
    a magnetic field emitter secured to said tool; and
    a magnetic field sensor to capture and to transfer to said computer the signal of said field emitters on said tool and on the at least on anatomical structure;
        wherein said computer uses said signals to determine the position of said anatomical structure and the position of said tool.

6. An interactive surgical system as recited in claim 1, wherein said position sensing system includes:
- at least one reference assembly secured to the at least one anatomical structure;
- a reference assembly secured to said tool; and
- a camera to capture and to transfer to said computer the image of said reference assemblies on said tool and on the at least one anatomical structure;
    - wherein said computer uses said image to determine the position of said anatomical structure and the position of said tool.

7. An interactive surgical system as recited in claim 1, wherein said output device includes a display monitor.

8. An interactive surgical system as recited in claim 1, wherein said output device includes three-dimensional display goggles.

9. An interactive surgical system as recited in claim 1, further comprising at least one input device, connected to said computer.

10. An interactive surgical system as recited in claim 9, wherein said at least one input device is selected from the group consisting of a mouse, a keyboard, a touch screen and a voice recognition system.

11. An interactive surgical system as recited in claim 1, wherein the at least one anatomical structure includes bones.

12. An interactive user interface for a computer system to assist a surgery on an anatomical structure, said user interface comprising:
- a tool;
- an output device connected to said computer; said output device being configured to display a three-dimensional model of each of the at least one anatomical structure and a three-dimensional model of said tool with a user-selectable level of opacity; and
- a position sensing system connected to the computer; said position sensing system being configured to register the position of said tool and the position of each of the at least one anatomical structure and to transfer these positions to the computer;
    - whereby, in operation, the computer, using said positions of said tool and of the at least once anatomical structure, is configured to determine virtual positions of said models of each of the at least one anatomical structures and of said tool and to control said output device to display said models of each of said anatomical structure and of said tool at their respective virtual positions.

13. An interactive user interface as recited in claim 12, wherein said position sensing system includes:
- at least one magnetic field emitter secured to the at least one anatomical structure;
- a magnetic field emitter secured to said tool; and
- a magnetic field sensor to capture and to transfer to said computer the signal of said field emitters of said tool and of the at least one anatomical structure;
    - wherein said computer uses said signals to determine the position of said anatomical structure and the position of said tool.

14. An interactive user interface as recited in claim 12, wherein said position sensing system includes:
- at least one reference assembly secured to the at least one anatomical structure;
- a reference assembly secured to said tool; and
- a camera to capture and to transfer to the computer the image of said reference assemblies on said tool and on the at least one anatomical structure.

15. An interactive user interface as recited in claim 12, wherein said output device is selected from the group consisting of a display monitor and three-dimensional display goggles.

16. An interactive user interface as recited in claim 12, wherein said tool is an awl.

17. An interactive user interface as recited in claim 12, further comprising at least one input device connected to said computer.

18. An interactive user interface as recited in claim 17, wherein said at least one input device is selected from the group consisting of a mouse, a keyboard, a touch screen and a voice recognition system.

19. A method to assist a surgical procedure on at least one anatomical structure, said method comprising:
- providing a position sensing system;
- providing a tool to perform a surgical procedure on the aty least one anatomical structure;
- using the position sensing system to register the relative position of the tool and of each of the at least one anatomical structure;
- using said relative position of said tool and of each of the at least one anatomical structure to compute respective virtual positions of each of the at least one anatomical structure and of said tool;
- providing an output device;
- inputting a user-selected level of opacity;
- display on the output device a first view including a transparent three-dimensional computer model of each of the at least one anatomical structure and a three-dimensional computer model of the tool at said respective virtual positions, the transparent model having a level of opacity dependent on the inputted user-selected level of opacity.

20. A method as recited in claim 19, further comprising using an input device to select a cutting plane on said at least one view.

21. A surgical procedure method as recited in claim 20, further comprising displaying on said output device a second view corresponding to said cutting plane; said second view including said transparent three-dimensional computer model of each of the at least one anatomical structure and said three-dimensional computer model of the tool at said respective virtual positions.

* * * * *